United States Patent
Valstar et al.

(10) Patent No.: US 12,135,943 B1
(45) Date of Patent: Nov. 5, 2024

(54) MOOD- AND MENTAL STATE-AWARE INTERACTION WITH MULTIMODAL LARGE LANGUAGE MODELS

(71) Applicant: Blueskeye AI Ltd, Nottingham (GB)

(72) Inventors: Michel François Valstar, Nottingham (GB); Anthony Brown, Nottingham (GB); Mani Kumar Tellamekala, Nottingham (GB)

(73) Assignee: Blueskeye AI Ltd, Nottingham (GB)

( * ) Notice: Subject to any disclaimer, the term of this patent is extended or adjusted under 35 U.S.C. 154(b) by 0 days.

(21) Appl. No.: 18/636,434

(22) Filed: Apr. 16, 2024

Related U.S. Application Data

(60) Provisional application No. 63/496,725, filed on Apr. 18, 2023.

(51) Int. Cl.
*G06F 40/30* (2020.01)
*A61B 5/024* (2006.01)
*G06V 40/16* (2022.01)

(52) U.S. Cl.
CPC .............. *G06F 40/30* (2020.01); *A61B 5/024* (2013.01); *G06V 40/174* (2022.01)

(58) Field of Classification Search
None
See application file for complete search history.

(56) References Cited

U.S. PATENT DOCUMENTS

| | | | |
|---|---|---|---|
| 10,552,977 B1 | 2/2020 | Theis | |
| 10,594,757 B1 | 3/2020 | Shevchenko | |
| 10,960,838 B2 | 3/2021 | Sobhany | |
| 11,430,467 B1 * | 8/2022 | Vasudevan | G10L 25/63 |
| 11,461,952 B1 * | 10/2022 | Bosnak | G06F 40/30 |

(Continued)

FOREIGN PATENT DOCUMENTS

| | | |
|---|---|---|
| CN | 109171773 | 1/2019 |
| EP | 3451209 A1 | 3/2019 |

(Continued)

OTHER PUBLICATIONS

Piferi, Francesco. "Chatcare: an emotional-aware conversational agent for assisted therapy." (2022). (Year: 2022).*

(Continued)

*Primary Examiner* — Douglas Godbold
(74) *Attorney, Agent, or Firm* — Koffsky Schwalb LLC; Mark I. Koffsky

(57) ABSTRACT

A system using large language models (LLMs) with multimodal inputs that has a low latency (within 500 ms) response time is described. This low latency produces a response that leads to a more engaging and empathetic user experience with all calculations done on consumer hardware. In so doing, the LLM derives the emotional state of the user using message sentiment analysis and/or face behavior and/or voice parameters that leads to a more engaging and empathetic user experience. This occurs by reviewing: (a) the user's mood state while providing an input prompt to the LLM in the current turn; (b) the user's mood and mental states while reacting to the LLM's response in the previous turn; (c) the sentiment of the LLM's response in the previous turn; and (d) the desired user mood and mental state as determined by the system's empathetic goal.

8 Claims, 3 Drawing Sheets

(56) References Cited

U.S. PATENT DOCUMENTS

| | | | |
|---|---|---|---|
| 11,632,456 B1* | 4/2023 | Mevorah | H04M 1/72454 455/420 |
| 11,869,535 B1* | 1/2024 | Bahadori | G10L 25/63 |
| 2010/0042401 A1* | 2/2010 | Ascoli | G06F 40/247 704/10 |
| 2015/0313530 A1 | 11/2015 | Kodra | |
| 2017/0238859 A1 | 8/2017 | Sadowsky | |
| 2017/0365277 A1* | 12/2017 | Park | G10L 15/1815 |
| 2018/0144761 A1 | 5/2018 | Amini | |
| 2018/0357286 A1 | 12/2018 | Wang | |
| 2018/0373979 A1 | 12/2018 | Wang | |
| 2019/0354879 A1 | 11/2019 | Van Rensburg | |
| 2019/0385711 A1 | 12/2019 | Shriberg | |
| 2020/0090542 A1 | 3/2020 | Clevenger | |
| 2020/0104616 A1 | 4/2020 | El Kaliouby | |
| 2020/0202887 A1* | 6/2020 | Modi | G10L 15/22 |
| 2020/0265294 A1 | 8/2020 | Kim | |
| 2020/0302952 A1* | 9/2020 | Pinkus | H04W 4/80 |
| 2021/0201078 A1 | 7/2021 | Yao | |
| 2022/0129687 A1 | 4/2022 | Munir | |
| 2022/0253676 A1 | 8/2022 | Valstar | |
| 2023/0290505 A1 | 9/2023 | Valstar | |
| 2024/0054794 A1 | 2/2024 | Valstar | |

FOREIGN PATENT DOCUMENTS

| | | |
|---|---|---|
| EP | 3621276 | 3/2020 |
| WO | 2019103484 | 5/2019 |

OTHER PUBLICATIONS

Zhong, Peixiang, Di Wang, and Chunyan Miao. "An affect-rich neural conversational model with biased attention and weighted cross-entropy loss." Proceedings of the AAAI Conference on Artificial Intelligence. vol. 33. No. 01. 2019. (Year: 2019).*

Zhong, Peixiang, et al. "Care: Commonsense-aware emotional response generation with latent concepts." Proceedings of the AAAI Conference on Artificial Intelligence. vol. 35. No. 16. 2021. (Year: 2021).*

Bao, Fang, Michael Neumann, and Ngoc Thang Vu. "CycleGAN-Based Emotion Style Transfer as Data Augmentation for Speech Emotion Recognition." Interspeech. 2019. 5 pages.

Blaz Meden et al: R&-Same-Net: k-Anonymity with Generative Deep Neural Networks for Face Deidentification. Entropy, vol. 20, No. 1, Jan. 13, 2018 (Jan. 13, 2018), p. 60. XP055730554, DOI: 0.3390/e20010060 Sections 3.2, 3.3, 3.4, 4, 1 and 4.6; Algorithm 1; figure 3.

Chhabra, et al., "Anonymizing k-Facial Attributes via Adversarial Perturbations", Proceedings of the Twenty-Seventh International Joint Conference on Artificial Intelligence (IJCAI-18), Jul. 2018, 7 pgs.

Dasari et al., Evaluation of biases in remote photoplethysmography methods, npj Digital Medicine (2021) 4:91, 13 pages.

Guo et al, "2018 37th Chinese Control Conference (CCC)", published Jul. 2018, IEEE, pp. 9356-9361, Guo et al, "Integrating Diversity into Neural-Network-Based Face Deidentification".

Hao-Yu Wu et al., Eulerian Video Magnification for Revealing Subtle Changes in the World, ACM Transactions on GraphicsVolume 31, Issue 4, Jul. 2012 Article No. 65, pp. 1-8.

IEEE transactions on Knowledge and Data Engineering, vol. 17, No. 2, 2005, Newton et al., "Preserving privacy by de-identifying face images", pp. 232-243.

International Search Report and Written Opinion from PCT Application PCT/GB2020/051521 dated Sep. 25, 20202, 12 pgs.

IPRP for PCT/GB2021/051904 (Jan. 24, 2023) 10 pages.

ISR for PCT/GB2023/052112 (Nov. 15, 2023), 26 pages.

James A Russell, A Circumplex Model of Affect, Journal of Personality and Social Psychology vol. 39, No. 6, 1161-1178 (1980).

Karras, Tero, Samuli Laine, and Timo Aila. "A style-based generator architecture for generative adversarial networks." Proceedings of the IEEE/CVF conference on computer vision and pattern recognition. Mar. 29, 2019. 12 pages.

Kumar, Abhinav, et al. "Luvli face alignment: Estimating landmarks' location, uncertainty, and visibility likelihood." Proceedings of the IEEE/CVF Conference on Computer Vision and Pattern Recognition. 2020. 18 pages.

Li et al., Learning Motion-Robust Remote Photoplethysmography through Arbitrary Resolution Videos, arXiv:2211.16922v3, Dec. 2, 2022, 11 pages.

Martinez, et al., "Automatic Analysis of Facial Actions: A Survey", IEEE Transactions on Affective Computing, vol. 8, No. X, 2017, 23 pgs.

Meden, et al. "Face Deidentification with Generative Deep Neural Networks", IET Signal Processing, May 2017, 18 pgs.

Newland, Real-time remote photoplethysmography using a webcam and graphical user interface (https://www.jimmynewland.com/wp/research/remote-ppg-gui/, accesed Apr. 18, 2023) 15 pages.

Pan et al, Mar. 27, 2019, "k-Same-Siamese-GAN" arxiv.org [online], Available from: https://arxiv.org/abs/1904.00816v1 [Accessed Nov. 21, 2019] 8 pages.

Ren et al, "Proceedings of the European Conference on Computer Vision (ECCV)", published 2018, ECCV, pp. 620-636, Ren et al, "Learning to anonymize faces for privacy preserving action detection".

Sanchez et al., "Triple consistency loss for pairing distributions in GAN-based face synthesis", Computer Vision Laboratory, The University of Nottingham, Paper, accessed Nov. 8, 2018, 10 pgs.

Search Report from GB Application GB1909003.4 dated Nov. 26, 2019, 4 pgs.

Seyed Ali Osia et al, "A Hybrid Deep Learning Architecture for Privacy-Preserving Mobile Analytics", arxiv.org, Cornell University Library, 201 Olin Library Cornell University Ithaca, NY 14853, (Mar. 8, 2017), XP081565752, 12 pages.

Vicente P Minotto et al: "Audiovisual Voice Activity Detection Based on Microphone Arrays and Color Information", IEEE Journal of Selected Topics in Signal Processing, IEEE, US, vol. 7, No. 1, Feb. 1, 2013, pp. 147-156.

W Bailer, "International Conference on Multimedia Modeling", published Jan. 2019, Springer, pp. 169-177, W Bailer, "Face Swapping for Solving Collateral Privacy Issues in Multimedia Analytics".

Yuezun Li et al, "De-identification without losing faces", arxiv.org, Cornell University Library, 201 Olin Library Cornell University Ithaca, NY 14853, (Feb. 12, 2019), XP081027993, 7 pages.

Marta Garnelo et al., Neural Processes, arXiv:1807.01622v1 [cs.LG] Jul. 4, 2018.

Search Report for GB2011453.4, Feb. 3, 2021 (2 Pages).

Alnuhait et al., FaceChat: An Emotion-Aware Face-to-face Dialogue Framework, Arxiv.org, Mar. 8, 2023, XP091460100 (8 pages).

EPO Office action for Application No. 21751805.5, dated Jun. 25, 2024 (7 pages).

ISR and WO for PCT/GB2024/050996, Jun. 24, 2024 (20 oages).

Office Action (Non-Final Rejection) dated Jul. 30, 2024 for U.S. Appl. No. 17/596,996 (pp. 1-17).

Warriner, Amy Beth et al., Norms of valence, arousal, and dominance for 13,915 English lemmas, Behavior Research Methods, vol. 145, No. 4, Dec. 1, 2013 (17 pages).

* cited by examiner

MOOD- AND MENTAL STATE-AWARE INTERACTION WITH MULTIMODAL LARGE LANGUAGE MODELS

PRIOR APPLICATIONS

This application claims the benefit of the following application, which is incorporated by reference in its entirety:
U.S. Provisional Patent Application No. 63/469,725, filed on Apr. 18, 2023.

FIELD OF THE DISCLOSURE

The present disclosure relates generally to improved techniques to improve the multimodal outputs of Large Language Models (LLMs) using mood and mental states measured from expressive behavioral and linguistic cues from multimodal inputs.

BACKGROUND

LLMs such as ChatGPT, Llama and others are language models having the ability to achieve general-purpose language generation and other natural language processing tasks such as classification. LLMs acquire these abilities by learning statistical relationships from text documents during a computationally intensive self-supervised and semi-supervised training process. LLMs may be used for text generation, a form of generative artificial intelligence (AI), by taking an input text and repeatedly predicting the next token or word.

It is desirable to improve the text outputs of Large Language Models (LLMs, e.g., ChatGPT, Llama, etc.) to improve user experience and engagement by using mood measured from expressive behavioral and linguistic cues from multimodal inputs. This approach seeks to combine the linguistic and paralinguistic components extracted from a multimodal input to compose a mood-aware input prompt to the LLM.

SUMMARY

Described herein is a system using LLMs with multimodal inputs that has a low latency (within 500 ms) response time. This low latency is required for a response that leads to a more engaging and empathetic user experience with all computations done on consumer hardware. In so doing, the system infers the user's mood and mental states from facial expressions, voice features, text sentiment and physiological measurements captured while the user is interacting with the LLM. Guided by the inferred mood and mental states, the system customizes the LLM input prompt to create a more engaging and empathetic interactive experience by considering:
 (a) the user's mood state while providing an input prompt to the LLM in the current turn;
 (b) the user's mood and mental states (e.g., confusion) while reacting to the LLM's response in the previous turn;
 (c) the sentiment of LLM's response in the previous turn; and
 (d) the desired user mood and mental state as determined by the system's empathetic goal.

BRIEF DESCRIPTION OF THE DRAWINGS

The accompanying figures, where like reference numerals refer to identical or functionally similar elements throughout the separate views, together with the detailed description below, are incorporated in and form part of the specification, serve to further illustrate embodiments of concepts that include the claimed invention and explain various principles and advantages of those embodiments.

Figure 1:
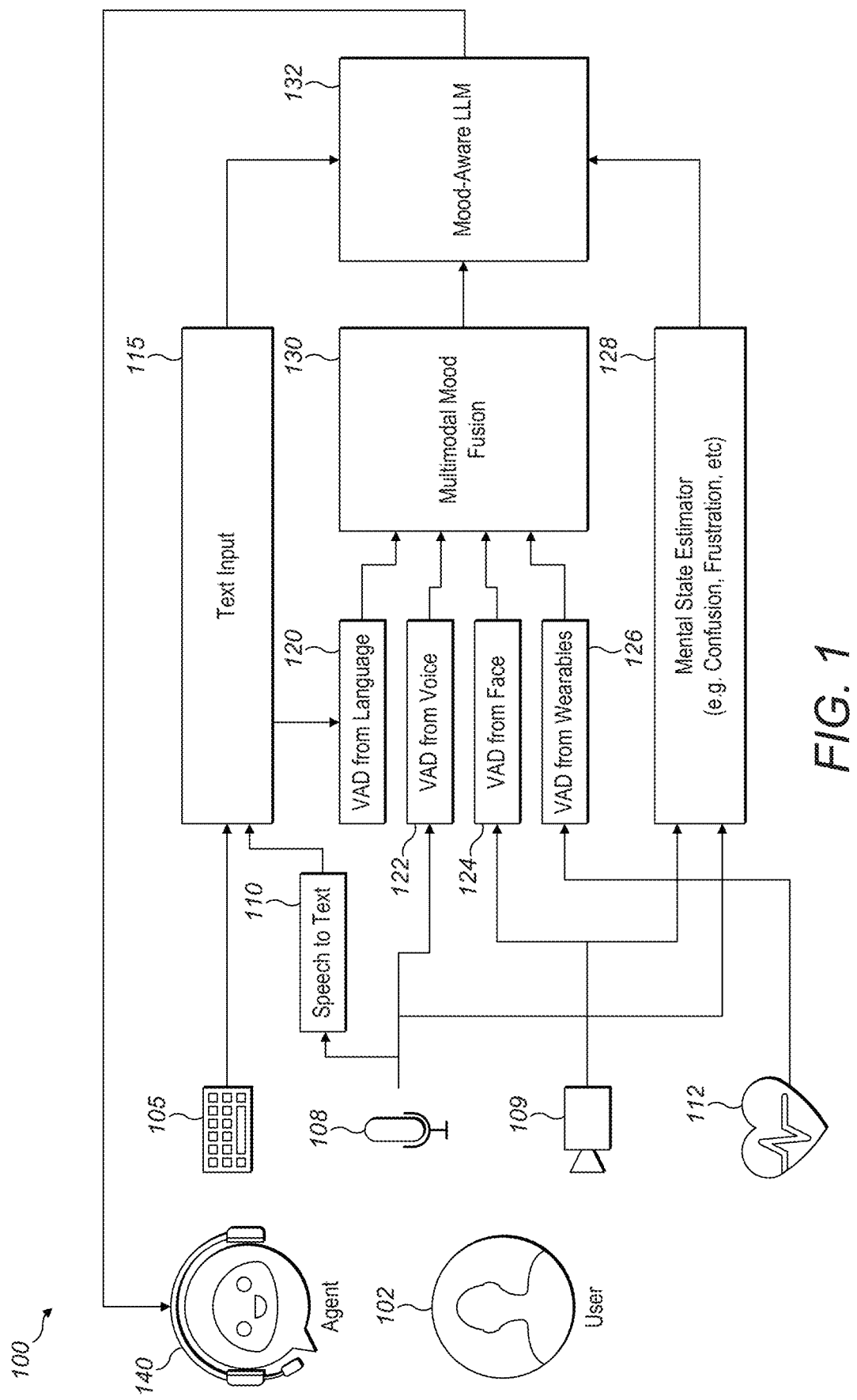
FIG. 1 shows a schematic of a system diagram of mood and mental state-aware interaction with multimodal LLMs.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

I. The VAD Model and its Use in LLMS

A. The VAD Model

A popular model used in the field of affective computing is the Valence-Arousal-Dominance (VAD) model (also called the Pleasure-Arousal-Dominance (PAD) model). In these models, the X, Y, and Z axes span from −1 to 1 and may be defined as follows:

Valence—How pleasant the subject feels on a range from −1 to 1. Here, −1 means the subject is feeling very negative/unpleasant, and 1 means the subject is feeling very positive/pleasant.

Dominance-How much control the subject has over what the subject feels on a range from −1 to 1. Here, −1 means the subject is feeling no control of the subject's emotion, and 1 means the subject is feeling total control of the subject's emotion.

Arousal-How engaged or alert a subject feels on a range from −1 to 1. Here, −1 means that a subject is on the calmer or sleepier extreme, and 1 means the subject is on the active and energetic extreme.

One underlying concept behind the model is that emotions may be defined in different combinations of these 3 dimensions.

B. LLMs

This disclosure defines "mood" as the temporal combination of emotional (for example: excited, frustrated, dejected) and cognitive state (for example: confused, drowsy) for the LLM user.

An empathetic mood aware LLM has an empathetic goal to achieve a change in mood in the user. This goal may be to maintain user mood, to achieve a higher valence, a higher arousal, a lower arousal (all relative to the current user mood) or to bring a user in a specific region in the valence-arousal-dominance space. Based on the empathic mood aware LLM's goal, it sets the target user mood in the VAD space and computes the output that is expected to get the user to that mood.

An empathetic mood aware LLM must respond quickly, under 500 ms (a human response latency is on average 200 ms) and this 500 ms response latency has experimentally been found acceptable. This may not be presently achievable with a multimodal LLM that takes video and audio as input, as processing the video is computationally expensive and introduces latency. The goal in this disclosure is to provide a low-latency response (in <500 ms).

Improvement of an output is measured in terms of the distance $d_m$ between a user's apparent mood $m_u$ and to the target mood $m_t$, with the target mood a function of the apparent user mood $m_u$ and the LLM's empathic goal setting $s_e$:

$$d_m = m_t - m_u;$$

$$m_t = f(m_u, s_e).$$

The LLM outputs a response y that is emotionally congruent with its empathetic goal. The mood value of the LLM output equals $m_r$ and should be as close as possible to the empathetic goal and the user mood $m_t = f(m_u, s_e)$. Empathetic goals may be mimicking the user mood, improving user mood, calming user mood, etc. Every empathetic goal $s_e$ changes the way f operates on $m_u$.

To facilitate a mood aware interaction with LLMs, a prompt customization module is developed. This module takes estimates of users' mood and mental states from face, voice, text, and physiological signals to calculate $m_u$ and the empathetic goal $s_e$ to return a customized text prompt $y = g(m_t)$.

The LLM may output text, speech, or an animated anthropomorphic face with speech.

The LLM response mood value $m_r$ is estimated using the multimodal mood fusion module.

To achieve the user mood over more than one response, the empathetic mood aware LLM must know the mood of the last n conversational turns (where n is a small number) and compare this against the target mood. The mood aware LLM takes as input the user mood for the last n turns, the LLM output mood, and the user target mood to create the Mood-Aware LLM output for the next agent conversational turn.

User mood ($m_{u,i}$) and LLM response mood ($m_{r,i}$) states of last n conversational turns are stored as [($m_{u,i}$, $m_{r,i}$)] for i=−n: 0, where i=0 is the current turn index.

Information from all modalities may be fused using a conversion context aware fusion technique to improve the user emotional state recognition.

This customized prompt drives the response for the LLM that may be improved by injecting emotion information into the prompt allowing the LLM to tailor its response.

The LLM may be running on the users computing device or as a cloud service.

Video and audio of the users may be captured using standard camera and microphone on a computing device while they are interacting with the system.

Physiological signals may be captured via non-contact techniques such as (without limitation) photoplethysmography (PPG) and pupillometry via the camera, or with skin contact sensors via wearable devices such as (without limitation) smart watches, smart rings, and other sensors.

II. Diagrams of a Mood and Mental State-Aware Interaction with Multimodal Large Language Models Turning to FIG. 1, shown is a schematic 100 of a system diagram of mood and mental state-aware interaction with multimodal LLMs. The system has inputs related to text from a keyboard input 105, audio input 108, visual input 109, and biometrics input 112, all from a User 102. The text from the keyboard input 105 is fed into a Text Input module 115, along with a Speech to Text conversion module 110 of the audio input 108. The output of the Text Input module is fed into the VAD from Language module 120. The audio input 108 is fed into the VAD from Voice module 122, and into the Mental State Estimator module 128. The visual input 109 is fed into the VAD from Face module 124, and into the Mental State Estimator module 128. The biometric input 112 is fed into the VAD from Wearables module 126. The biometric input 112 may be obtained from any wearable on the person of the User 102, including headsets, armbands, leg bands, and the like.

The outputs of the VAD from Language module 120, VAD from Voice module 122, VAD from Face module 124, and VAD from Wearables module 126 are fed into the Multimodal Mood Fusion module 130. The output of the Multimodal Mood Fusion module 130 is fed into the Mood-Aware LLM 132, along with the output of the Mental State Estimator module 128, and the Text Input module 115. Finally, the result of the Mood-Aware LLM 132 is transmitted to the Agent 140, which then performs the function of communicating with the User 102.

Figure 2:
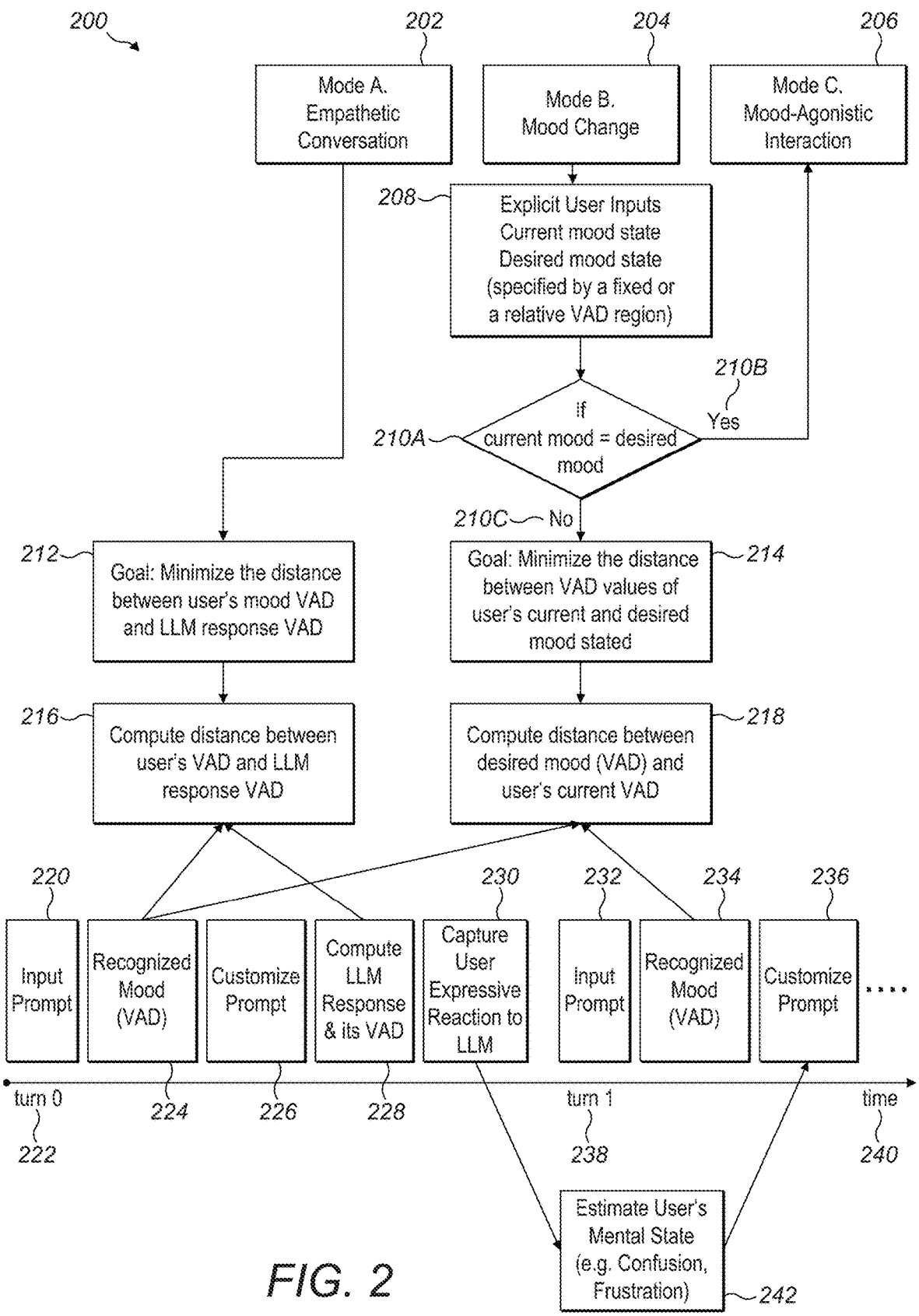
FIG. 2 shows a is a schematic of a state diagram of a mood and mental state-aware interaction with multimodal LLMs.

Turning to FIG. 2, shown is a is a schematic 200 of a state diagram of a mood and mental state-aware interaction with multimodal LLMs. Here, Mode A (Empathetic Conversation) 202 for the LLM results in the goal of minimizing the distance between the user's mood VAD and the LLM responsive VAD 212. This is accomplished by a module for computing the distance between the user's VAD and the LLM responsive VAD ("Empathetic Conversation Computation Module") 216.

Mode B (Mood Change) 204 begins with explicit user inputs for determining a current mood state and a desired mood state (specified by a fixed or a relative VAD region) 208. A decision is required to determine if the current mood equals the desired mood 210A. If yes 210B, then Mode C (Mood-Agnostic Interaction) 206 begins. If no 210C, then this results in the goal of minimizing VAD values of the user's current and desired mood states 214. This is accomplished by a module for computing the distance between the desired mood (VAD) the user's current VAD ("Mood Change Computation Module") 218.

A timeline 240 showing processes in turn 0 222 comprises an Input Prompt 220, which leads to a Recognized Mood (VAD) 224, which leads to a Prompt Customization module 226, which leads to Compute LLM and its VAD 228, which leads to a Capture User Expressive Reaction to LLM 230. The output of the Recognized Mood (VAD) 224 is processed by the Empathetic Conversation Computation Module 216 and the Mood Change Computation Module 218. The output of the Compute LLM and its VAD 228 is processed by the Empathetic Conversation Computation Module 216.

Processes in turn 1 238 of the timeline 240 comprise a second Input Prompt 232, which leads to a second Recognized Mood (VAD) 234, which leads to a second prompt Customization module 236, and so on. The output of the second Recognized Mood (VAD) 234 is processed by the Mood Change Computation Module 218. Finally, the output of the Capture User Expressive Reaction to LLM 230 is processed by a Mental State Estimation module 242 that estimates a user's metal state (e.g., confusion, frustration), and that result is fed into the second prompt Customization module 236.

Figure 3:
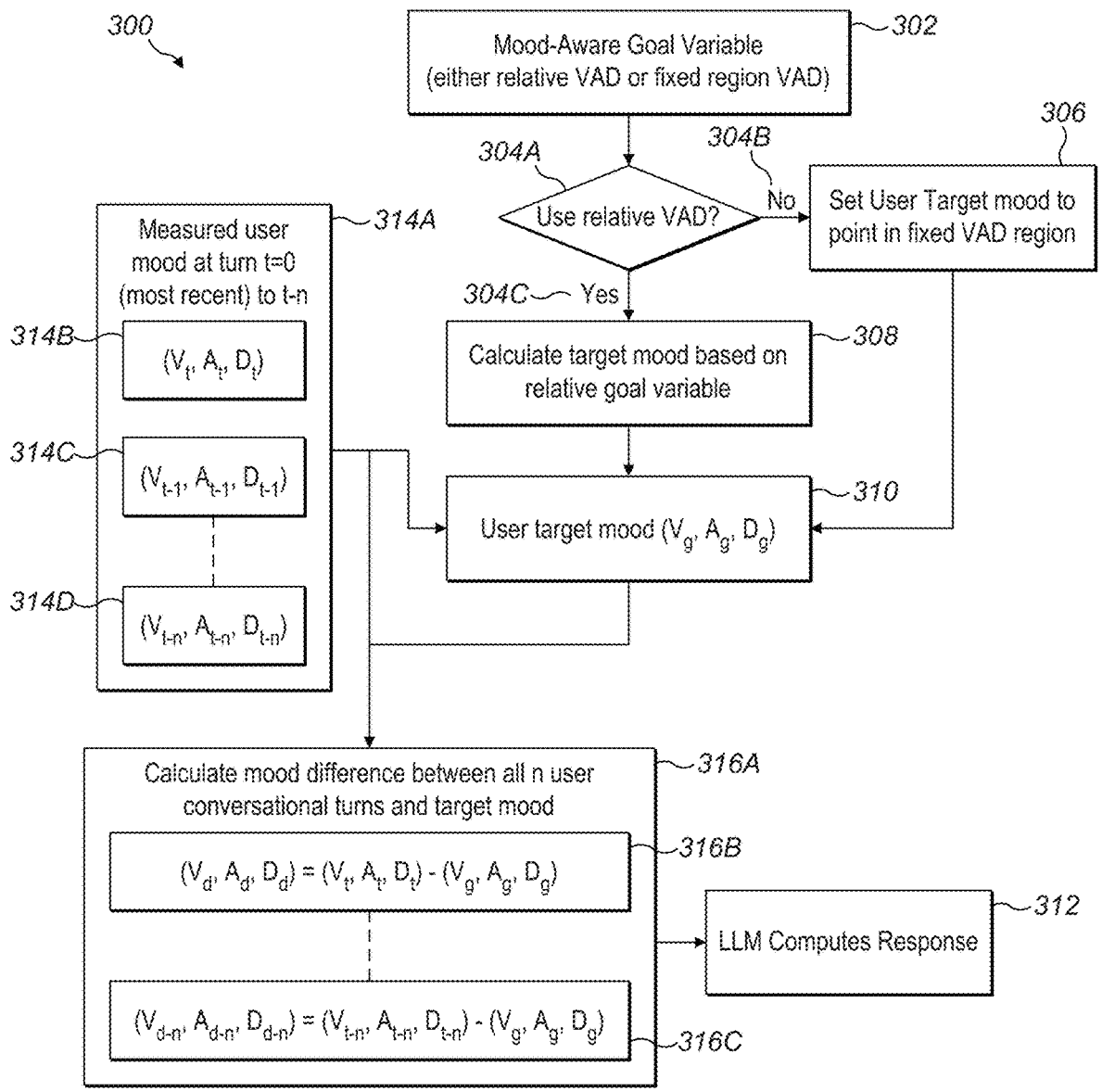
FIG. 3 shows a schematic of a computational flow diagram of a mood and mental state-aware interaction with multimodal LLMs.

Turning to FIG. 3, shown is a is a schematic 300 of a computational flow diagram of a mood and mental state-aware interaction with multimodal LLMs. In this flow diagram, the subscript g means a goal, the subscript d means a difference.

The flow diagram begins with a Mood-Aware Goal Variable module 302 (either relative VAD or fixed region VAD). The output of this a Mood-Aware Goal Variable module 302 leads to a decision as to whether to use relative VAD 304A. If yes 304C, then there is a calculation of a target mood based on relative goal variable 308, which is fed into a User target mood $(V_g, A_g, D_g)$ module 310. If no 304B, then there is a setting of a User target mood to point in a fixed VAD region, which is fed into a User target mood $(I_g, A_g, D_g)$ module 310. (The subscript g means a goal value of V, A, or D, as the case may be.)

Separately, there is a measured user mood at turn t=0 (most recent) to t−n 314A, which includes a series of VAD readings beginning with $(V_t, A_t, D_t)$ 314B, then $(V_{t-1}, A_{t-1}, D_{t-1})$ 314C, and so on until $(V_{t-n}, A_{t-n}, D_{t-n})$ 314D. This measurement is from turn t (the current turn) to turn t−n (the last n turns). For example, if the current turn index t is 10 and the value of n is 4, then the mood is measured for turns 10, 9, 8, 7, and 6. This result is fed into User target mood $(V_g, A_g, D_g)$ module 310, and—along with the output of the User target mood $(V_g, A_g, D_g)$ module 310—it is fed into the module that calculates the mood difference between all n user conversational turns and target mood 316A. This calculation begins with $(V_d, A_d, D_d)=(V_t, A_t, D_t)-(V_g, A_g, D_g)$ 316B and concludes with $(V_{d-n}, A_{d-n}, D_{d-n})=(V_{t-n}, A_{t-n}, D_{t-n})-(V_g, A_g, D_g)$ 316C. (The subscript d means the difference value of V, A, or D, as the case may be.) The results of the calculations are made available so that the LLM computes a response 312.

III. Module Descriptions

Further descriptions of the foregoing modules are described herein.

A. Speech to Text Module

The Speech to Text conversion module 110 transcribes an input voice signal into text in near-real time. This module may be implemented using a computationally light-weight edge-based automatic speech recognition model built for real time inference. Optionally, the speech recognition may use visual information to improve its accuracy. Optionally, the speech recognition may use visual information only to estimate what was said. Optionally, the visual information may be used to recognize the user and only process speech from the user and ignore speech from other people in the recording. Optionally, the user may directly enter the text input using the keyboard, bypassing the need for speech recognition. This direct input text or transcribed text from speech is first modulated by the user's mood and mental state and then fed as an input prompt into LLM.

B. Prompt

A prompt consists of a conversational message from the user to the system. A prompt is considered a single conversational turn. A turn/may consist of multiple words, sentences, or utterances. A prompt may include all non-verbal cues (facial expressions, tone of voice, gaze actions, etc.) in addition to the verbal cues.

C. Emotion Description

Expressed or apparent emotions may be modelled as points in a 3D continuous space constructed using valence, arousal, and dominance dimensions as used in Russell's dimensional affect theory of emotion. See James A Russell, A Circumplex Model of Affect, Journal of Personality and Social Psychology Vol. 39, No. 6, 1161-1178 (1980).

Russell's model suggests valence and activation are independent, bipolar dimensions. "Independent" means valence and activation are uncorrelated. "Bipolar" means that opposite emotions terms represent each of the opposite poles for valence and activation.

Other words used for valence and arousal are pleasure and activation. Optionally a different continuous emotion space may be used. Optionally a one or two-dimensional subspace may be used. Optionally a higher dimensional continuous emotion space may be used. Expressed or apparent emotion may be estimated using machine learning systems, by asking observers to estimate the emotion, by asking the person expressing the emotion to rate their own emotion. Expressed emotion may be described either as a single value for a specific time unit (e.g., 10 ms), or per conversational unit (e.g., word, sentence, turn, utterance). In this disclosure, "VAD" means any emotion description defined in this paragraph.

D. Unimodal Mood Inference Modules

Unimodal Mood Inference Module may output a temporal aggregate of expressed emotions to the user's apparent and/or felt mood state predictions from each modality, i.e., face, voice, text, and physiological signals, separately. These modality-wise mood predictions may be fused into a single apparent mood state in the Multimodal Mood Fusion module. Alternatively, a person may input the mood to the system. This person may be someone other than the user.

Mood may be represented as a value on the VAD scale, or it may be simplified to a unidimensional scale of [−1.0, 1.0]. Mood may be computed through temporal aggregation of expressed emotion information embedded in the input prompt. The prompt may include non-verbal data from face, voice, and physiological signals.

To estimate mood from each modality, first modality-wise expressive features (e.g., Facial Action Unit intensities, voice Low Level Descriptors, etc.) may be extracted, and then the scores of VAD may be predicted on a given time unit basis (per frame, word, sentence, turn, utterance). These per-time-unit VAD predictions may then be temporally aggregated into modality-wise mood scores for the whole prompt. The variance of the VAD predictions may be used as a proxy for computing modality-wise confidence scores of their corresponding mood predictions.

1. Expressed Emotion from the Language Module

Expressed emotion from the Language module 120 may be implemented in a number of ways to estimate VAD in near real-time on consumer hardware such as a mobile phone. VAD may be estimated from language using a predefined emotion labelled natural language lexicon to predict the expressed emotion values of selected emotionally salient words in the text input. VAD may be estimated from language using a computationally lightweight Machine Learning model capable of running in real-time on consumer hardware. This may take a sequence of word embedding vectors as inputs to predict expressed emotion values on either per-word or per-utterance basis.

The model may be trained to automatically identify the emotional words and fuse the temporal context for improved expressed emotion predictive accuracy.

2. Expressed Emotion from the Face Module

Expressed emotion from the Face module 124 estimates VAD values by analyzing the user's facial expressive cues and their temporal dynamics in the input video in near real-time on consumer hardware such as a mobile phone. To meet the latency requirements of the proposed system, implementing this module requires a well-optimized facial expression analysis model pipeline composed of a face bounding box detector, a facial landmark detector, an expression recognition model for extracting expressive behavioral cues on a fixed time-unit basis, and an emotion prediction model for mapping those cues and their temporal dynamics to different points to VAD. Here, the expression recognition model may be implemented through either predicting the explicit facial muscle activations using Action Unit intensities directly or predicting a facial expression embedding vector that implicitly encodes different expressive cues. The expressed emotion prediction model may take per-frame outputs of the expression recognition module to compute the expressed emotion scores either on a fixed time basis measured in ms (using a sequence to sequence mapping) or a variable length basis (e.g., per word, sentence, or utterance), depending on the temporal prediction architecture. Optionally, the module may use visual cues from body pose to improve expressed emotion estimation. Optionally, the module may detect vital signs including pupillometry, heart rate, heart rate variability, and breathing rate from visual cues to improve expressed emotion estimation.

3. Expressed Emotion from the Voice Module

Expressed emotion from the Voice module 122 may be implemented using a simple regression model that takes hand-crafted features as inputs, (e.g., voice Low-Level Descriptors (LLDs) such as Mel Frequency Cepstral Coefficients (MFCCs)) to estimate VAD in near real-time on consumer hardware such as a mobile phone.

A voice based expressed emotion model may be trained to output the emotion values on a per-utterance basis. A voice based expressed emotion model may use Wav2Vec like deep learning architecture to predict expressed emotion values directly from the raw audio waveform input. A voice based expressed emotion model may use deep neural networks, such as a transformer model, a recurrent neural network, or any other artificial neural network that may predict expressed emotion from voice data.

4. Expressed Emotion from the Wearable Sensors Module

Expressed emotion from the Wearables module 126 aims to infer the user's "felt" mood state by sensing physiological arousal levels from heart rate signals and valence levels from heart rate variability patterns. Given the limitations of the face, voice, and text modalities in predicting low-arousal emotion states, the expressed emotion predictions from physiological parameters may complement the emotion information extracted from the aforementioned modalities. The Wearable module 126 expressed emotion prediction performance requires establishing a user-specific "neutral" baseline of these physiological signals for expressed emotion, which may be done for valence, arousal, and dominance dimensions separately.

E. The Multimodal Mood Fusion Module

The Multimodal Mood Fusion module 130 may use the confidence scores of these unimodal prediction models to fuse modality-wise mood predictions into a single mood score, for an accurate estimation of the user's mood state. These confidence scores may be used as proxy measures to indicate the reliability of different modalities for mood sensing. Fusion may be implemented as a weighted average (linear regression) of all the unimodal mood estimation modules. Fusion may be implemented as a (recurrent) neural network that takes the unimodal mood estimation modules output as input. Fusion may be implemented as a support vector machine that takes the unimodal mood estimation modules output as input. Any of the above methods may use intermediate results of a unimodal mood estimation module as (additional) input, such as the outputs of the penultimate layer of an artificial neural network.

F. The Prompt Customization Module

The Prompt Customization modules 226, 236 take as input the transcribed text output from the speech-to-text module along with the multimodal mood scores. For turn i>=1, the estimated mental state of the user using the Mental State Estimation module 242 is additionally provided as input to this module.

The Prompt Customization modules 226, 236 encode the user's mood and mental state information into the text prompt. These modules may be implemented by a rule-based expert system in which a predefined look up table is used to map a particular mood and/or mental state to a prompt customization type. The module may be implemented by fine-tuning the weights of a pre-trained LLM using a training set of desired mood targets $m_t$ and a cost function that penalizes outputs with a different mood value $(m_t-m_r)$. The module may be implemented with a second LLM following the original LLM where the second LLM is trained with a training set of desired mood targets $m_t$ and a cost function that penalizes outputs with a different mood value $(m_t-m_r)$.

G. The Mental State Estimation Module

The Mental State Estimation module 242 aims to capture the user's emotional reaction to the LLM output. For instance, "agreement", "confusion", and "frustration" are some commonly encountered mental states in interactions with digital assistants. This may be posed as a classification model that takes face and voice inputs captured during the user's response to the LLM output and returns a list of probability scores indicating the likelihood of different mental states. The classification may be done using any machine learning method.

Optionally, the estimated mental states and mood states may be directly fed into the Multimodal LLM, bypassing the need for a heuristically designed Prompt Customization modules 226, 236.

For the LLM to respond quickly under 500 ms, it is important that the mood estimation from high-dimensional input data (video and audio) is implemented in a resource-efficient manner. To speed up the mood inference step, these four unimodal mood modules may be executed in parallel as soon as their required input signals are extracted from a given multimodal input.

IV. Sample Input and Output

Exemplary input and output samples showing the difference between a generic LLM output and a mood aware LLM output are shown in Table 1

TABLE 1

| Input Text Prompt | Generic LLM Output | Mood Aware LLM Output |
|---|---|---|
| I'm feeling awful today. | I'm sorry to hear that. Is there anything I can help with? | I'm sorry to hear that you are feeling that way. It is common to experience a low mood |

TABLE 1-continued

| Input Text Prompt | Generic LLM Output | Mood Aware LLM Output |
|---|---|---|
| | | sometimes. There are things you can try that may help. Music also may help in uplifting your mod. |
| I'm feeling great today. | I'm glad to hear that. Is there anything I can help with? | I'm happy to hear that you are feeling great. To continue the positive mood, connecting with your friends and family may help. |
| I'm feeling very calm and relaxed now. | I'm glad to hear that you're feeling calm and relaxed. If there's anything specific you'd like assistance with or if you have any questions, feel free to let me know. | That's wonderful to hear! It sounds like you're having a fantastic day. Enjoy this feeling of calmness and relaxation, and take some time to fully appreciate the great mood you're in. If there's anything specific you'd like to talk about or do to keep this positive vibe going, feel free to share! |
| I'm getting annoyed with everything today. | I'm sorry to hear that you're feeling this way. It's important to take care of yourself when you're feeling frustrated. | I'm sorry to hear that you're feeling that way. Remember, tough times never last, but tough people do. Take a deep breath, focus on the positives in your life, and know that you have the strength to overcome any challenges that come your way. You are capable, resilient, and deserving of happiness. Keep going, and brighter days are ahead. You've got this! |
| I'm feeling very irritable today. | I'm sorry to hear that you're feeling irritable. Is there something specific that is bothering you, or is it a general feeling of irritability? | I'm sorry to hear that you're feeling irritable and in a bad mood. Remember that it's okay to have moments like this, and it's important to be kind to yourself during times of struggle. |

V. Innovations

Innovations of this disclosure include the following:

1. This system has low latency which is required for a responsive which leads to a more engaging and empathetic user experience with responses generated within 500 ms of the end of the user turn and all calculations done on consumer hardware.

2. Deriving the emotional state of the user using message sentiment analysis and/or face behavior and/or voice parameters leads to a more engaging and empathetic user experience.

3. Taking into account the emotional reaction to the last LLM prompt leads to a more engaging and empathetic user experience.

4. Taking into account the emotional reaction to the user emotional state while providing an input to the LLM leads to a more engaging and empathetic user experience.

5. Taking into account the emotional reaction to the last LLM prompt and emotional state while providing an input to the LLM leads to a more engaging and empathetic user experience.

VI. Additional Disclosure

Additional disclosure includes the following.

1. A system comprising:
a first module set comprising:
1) a first input prompt module having a first input prompt module output;
2) a first recognizing mood module using valence, arousal, and dominance to review the first input prompt module output, and create a first recognizing mood module output;
3) a first customizing prompt module to customize the first recognizing mood module output, and create a first customizing prompt module output;
4) a first computing large language model (LLM) response module using valence, arousal, dominance and the first customizing prompt module output to create a first computing LLM response output;
5) a first capturing module to determine an expressive reaction of a user to the first computing LLM response output;
a mental state estimator operating on the first computing LLM response output to create a mental state estimate output;
a second module set comprising:
1) a second input prompt module having a second input prompt module output;
2) a second recognizing mood module using valence, arousal, and dominance to review the second input prompt module output, and create a second recognizing mood module output;
3) a second customizing prompt module to customize the second recognizing mood module output based at least in part on the mental state estimate output, and to create a second customizing prompt module output.

2. The system as in paragraph 1, wherein the first module set and the second module set are completed within 500 ms.

3. The system as in paragraph 2, wherein the first recognizing mood module output and the first computing LLM response output are used to compute distance between a responsive valence, arousal, and dominance of the user and a responsive valence, arousal, and dominance of the LLM.

4. The system as in paragraph 3, wherein the first module set and the second module set seek to substantially minimize the distance between a responsive valence, arousal, and dominance and the LLM's responsive valence, arousal, and dominance.

5. The system as in paragraph 1, wherein the first recognizing mood module output and the second recognizing mood module output are used to compute a distance between a current valence, arousal, and dominance of the user and a desired valence, arousal, and dominance of the user.

6. The system as in paragraph 5, wherein the first recognizing mood module and the second recognizing mood module seek to minimize the distance between a current valence, arousal, and dominance of the user and the desired valence, arousal, and dominance of the user.

7. The system as in paragraph 6, further comprising a current mood state and a desired mood state.

8. The system as in paragraph 7, wherein the current mood state does not equal the desired mood state.

9. A method comprising:
- a current turn preceding at least one prior turn, wherein the current turn comprises: deriving first valence, arousal, and dominance values from language of a user, wherein the language of the user is generated from at least one of speech of the user and text input of the user;
- deriving second valence, arousal, and dominance values from a voice of user;
- deriving third valence, arousal, and dominance values from a face of the user;
- deriving fourth valence, arousal, and dominance values from a wearable of the user;
- combining a mood state of the user based on the first valence, arousal, and dominance values, the second valence, arousal, and dominance values, the third valence, arousal, and dominance values, and the fourth valence, arousal, and dominance values to produce multimodal mood fusion values;
- estimating a mental state of the user based on the voice of the user and the face of the user to produce mental state estimated values; and
- generating a mood-aware response for an agent using a large language model (LLM) based on an estimated mood state of the user and an estimated mental state of the user.

10. The method as in paragraph 9, wherein the deriving steps, the combining step, the estimating step, and the generating step are completed within 500 ms.

11. The method as in paragraph 10, wherein the generating step is based on a second mood state of the user while providing an input prompt to the LLM in the current turn.

12. The method as in paragraph 10, wherein the generating step is based on the estimated mood state of the user and the estimated mental state of the user while reacting to a response of the LLM in the at least one prior turn.

13. The method as in paragraph 10, wherein the generating step is based on a response of the LLM in the at least one prior turn.

14. The method as in paragraph 10, wherein the generating step is based on a desired mood state and a desired mental state.

15. The method as in paragraph 10, wherein the generating step is based on user mood measurements from the at least one prior turn, which is used to establish a current user target mood.

16. The method as in paragraph 15, wherein the generating step is further based a calculating mood difference between the at least one prior turn and the current user target mood.

17. The method as in paragraph 10, wherein the generating step sets a mood-aware goal using relative valence, arousal, and dominance values by calculating user target mood based on relative goal variables.

18. The method as in paragraph 10, wherein the generating step sets user target mood using fixed valence, arousal, and dominance values.

19. The method as in paragraph 10, wherein the deriving first valence, arousal, and dominance values comprises using a predefined emotion labelled natural language lexicon to predict expressed emotion values of selected emotionally salient words.

20. The method as in paragraph 10, further comprising: identifying emotional words and fuses temporal context for expressed emotion predictive accuracy.

21. The method as in paragraph 10, wherein deriving the third valence, arousal, and dominance values from the face of the user comprises a facial expression analysis model pipeline using at least one of: a face bounding box detector, a facial landmark detector, an expression recognition model for extracting expressive behavioral cues on a fixed time-unit basis, and an emotion prediction model for mapping behavioral cues to different points on the third valence, arousal, and dominance values.

22. The method as in paragraph 10, wherein deriving the third valence, arousal, and dominance values from the face of the user comprises an expressed emotion prediction module computing expressed emotion scores on a fixed length basis.

23. The method as in paragraph 10, wherein deriving the third valence, arousal, and dominance values from the face of the user comprises an expressed emotion prediction module computing expressed emotion scores on a variable length basis.

24. The method as in paragraph 10, wherein deriving the third valence, arousal, and dominance values from the face of the user comprises detecting at least one of: pupillometry, heart rate, heart rate variability, and breathing rate from visual cues.

25. The method as in paragraph 10, wherein deriving the second valence, arousal, and dominance values from the voice of the user uses architecture to predict expressed emotion values directly from an audio waveform input.

26. The method as in paragraph 10, wherein deriving the fourth valence, arousal, and dominance values from the wearable of the user comprises sensing physiological arousal levels from heart rate signals and valence levels from heart rate variability patterns.

27. The method as in paragraph 26, further comprising establishing a user-specific neutral baseline of physiological signals for expressed emotion.

28. The method as in paragraph 10, wherein generating the mood-aware response further comprises a rule-based expert system implemented via a predefined look up table to map the estimated mood state of the user and the estimated mental state of the user to a prompt customization type.

29. The method as in paragraph 10, wherein generating the mood-aware response further comprises fine-tuning weights of the LLM using a training set of a desired mood value and a cost function that penalizes outputs with a different mood value.

30. The method as in paragraph 10, wherein generating the mood-aware response further comprises fine-tuning weights of a second LLM using a training set of a desired mood value and a cost function that penalizes outputs with a different mood value.

VII. Conclusion

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The term "coupled" as used herein is defined as connected, although not necessarily directly and not necessarily mechanically. A device or structure that is "configured" in a certain way is configured in at least that way but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

We claim:

1. A system comprising:
   a first module set comprising:
   1) A first input prompt module having a first input prompt module output;
   2) A first recognizing mood module using valence, arousal, and dominance to review the first input prompt module output, and create a first recognizing mood module output;
   3) A first customizing prompt module to customize the first recognizing mood module output, and create a first customizing prompt module output;
   4) A first computing large language model (LLM) response module using valence, arousal, dominance and the first customizing prompt module output to create a first computing LLM response output;
   5) A first capturing module to determine an expressive reaction of a user to the first computing LLM response output;
   a mental state estimator operating on the first computing LLM response output to create a mental state estimate output;
   a second module set comprising:
   1) A second input prompt module having a second input prompt module output;
   2) A second recognizing mood module using valence, arousal, and dominance to review the second input prompt module output, and create a second recognizing mood module output;
   3) A second customizing prompt module to customize the second recognizing mood module output based at least in part on the mental state estimate output, and to create a second customizing prompt module output.

2. The system as in claim 1, wherein the first module set and the second module set are completed within 500 ms.

3. The system as in claim 2, wherein the first recognizing mood module output and the first computing LLM response output are used to compute distance between a responsive valence, arousal, and dominance of the user and a responsive valence, arousal, and dominance of the LLM.

4. The system as in claim 3, wherein the first module set and the second module set seek to substantially minimize the distance between a responsive valence, arousal, and dominance and the LLM's responsive valence, arousal, and dominance.

5. The system as in claim 1, wherein the first recognizing mood module output and the second recognizing mood module output are used to compute a distance between a current valence, arousal, and dominance of the user and a desired valence, arousal, and dominance of the user.

6. The system as in claim 5, wherein the first recognizing mood module and the second recognizing mood module seek to minimize the distance between a current valence, arousal, and dominance of the user and the desired valence, arousal, and dominance of the user.

7. The system as in claim 6, further comprising a current mood state and a desired mood state.

8. The system as in claim 7, wherein the current mood state does not equal the desired mood state.

* * * * *